United States Patent [19]

Lampropoulos et al.

[11] Patent Number: 5,215,536
[45] Date of Patent: Jun. 1, 1993

[54] SELF-LOCKING CONTROL SYRINGE

[75] Inventors: Fred P. Lampropoulos; William Padilla, both of Salt Lake City; Arlin D. Nelson, Midvale, all of Utah

[73] Assignee: Merit Medical Systems, Inc., Salt Lake City, Utah

[21] Appl. No.: 792,203

[22] Filed: Nov. 13, 1991

[51] Int. Cl.⁵ .............................................. A61M 5/315
[52] U.S. Cl. ............................ 604/220; 604/218; 604/187
[58] Field of Search ............... 604/110, 187, 218, 220, 604/221, 222; 128/919, 763

[56] References Cited

U.S. PATENT DOCUMENTS

| | | | |
|---|---|---|---|
| 3,747,812 | 7/1973 | Karman et al. | 222/387 |
| 3,951,146 | 4/1976 | Chiquiar-Arias | 604/110 |
| 4,333,458 | 6/1982 | Margulies et al. | |
| 4,386,606 | 6/1983 | Tretinyak et al. | 604/220 |
| 4,610,672 | 9/1986 | Ewalt et al. | 604/220 |
| 4,711,637 | 12/1987 | Leigh et al. | 604/220 |
| 4,744,791 | 5/1988 | Egolf | 604/229 |
| 4,758,232 | 7/1988 | Chak | 604/220 |
| 4,840,616 | 6/1989 | Banks | 604/110 |
| 4,890,626 | 1/1990 | Wang | 128/752 |
| 4,925,449 | 5/1990 | Saez et al. | 604/227 |
| 4,929,238 | 5/1990 | Baum | 604/208 |
| 4,961,728 | 10/1990 | Kosinski | 604/110 |
| 4,973,310 | 11/1990 | Kosinski | 604/110 |

FOREIGN PATENT DOCUMENTS

| | | | |
|---|---|---|---|
| 8902287 | 3/1989 | World Int. Prop. O. | 604/110 |
| 8909331 | 10/1989 | World Int. Prop. O. | 604/110 |
| 9101768 | 2/1991 | World Int. Prop. O. | 604/110 |
| 9112039 | 8/1991 | World Int. Prop. O. | 604/110 |

Primary Examiner—C. Fred Rosenbaum
Assistant Examiner—Mark O. Polutta
Attorney, Agent, or Firm—Workman Nydegger Jensen

[57] ABSTRACT

A syringe for injecting medicinal fluids into a patient or aspirating fluids or tissue from a patient, wherein the syringe incorporates a self-locking mechanism on the plunger thus preventing the plunger from being withdrawn back into the barrel by the action of a vacuum in the syringe barrel. The self-locking mechanism is independent of the relative rotational relationship of the plunger with respect to the barrel. Unlocking may be effected by simply squeezing the self-locking mechanism on the plunger, no rotational force being necessary.

14 Claims, 5 Drawing Sheets

SELF-LOCKING CONTROL SYRINGE

BACKGROUND

1. Field of the Invention

The invention is in the field of syringes employed in the medical field, particularly those used for injecting fluids or for aspirating fluids or tissue under the influence of a vacuum, and most particularly those which employ a locking device.

2. The Related Technology

Syringes are used in the medical field both for injecting medications into a patient, for aspirating fluids and tissue from a patient, and for injecting or aspirating fluids in connection with other types of apparatus, as for example when preparation the balloon of a dilation catheter. In most such applications, whether the syringe is being used for injecting or aspirating, a vacuum is effected in the barrel of the syringe, although the reasons for the vacuum are quite different.

In the situation wherein the syringe is being used for injection will be described first. In this situation the barrel of the syringe is partially filled with a medicinal fluid and a hypodermic needle or equivalent is attached to the distal end of the barrel. The hypodermic needle is then inserted into the patient, with the intent of having the point of the needle inserted into a vein. However, it sometimes happens that the point of the needle is not within a vein, but, unknown to the doctor or nurse, is positioned within subcutaneous tissue. If the plunger of the syringe were then pushed into the barrel of the syringe the fluid would be injected into a wrong location, with perhaps disastrous results. In order to assure the proper positioning of the needle the practitioner normally follows the following procedure. The practitioner first injects the tip of the needle deliberately into subcutaneous tissue, and then withdraws the plunger partially from the barrel. This creates a vacuum in the barrel of the plunger distal to the piston head. The practitioner then follows through so as to inject the tip of the needle into the desired vein. If the needle tip is truly within the vein then a small amount o blood will be sucked into the barrel under the influence of the vacuum. Since the barrel wall is transparent the practitioner can see the blood, and then is assured that the vein has been found, and injection can proceed.

In the second situation noted above the practitioner is interested not in injecting a fluid into the patient but in aspirating fluid, or even tissue, from the patient. In this situation the practitioner creates a vacuum in the syringe as before and then follows through so as to insert the tip of the needle into the desired vein or tissue. The vacuum then causes fluid or tissue to be aspirated.

In the third situation described above where the syringe is used for injecting or aspirating fluids in connection with other types of apparatus, as in the case when the balloon of the dilation catheter is prepared, the syringe is connected to the catheter and tubing so that by withdrawing the syringe plunger, fluid is withdrawn from the balloon of the dilation catheter during the setup procedure. As in the other two situations mentioned above, when this is done a relatively strong vacuum is created within the barrel of the syringe which tends to exert a force on the syringe plunger that would otherwise pull the syringe plunger back into the barrel of the syringe unless the syringe plunger is restrained by grasping it tightly and holding it. Thus, the creation of a vacuum in the syringe under any one of the three kinds of situations described above tends to pull the plunger back into the syringe barrel unless some means is employed to prevent it.

With some syringes this means is supplied by the practitioner holding onto the shank of the plunger so as to prevent it from being drawn into the barrel of the syringe. However, this is awkward, and sometimes necessitates the use of two hands. Therefore, many syringes employ some form of a locking device whereby the practitioner can lock the plunger in place once the vacuum has been effected. However, these syringes almost universally require that the plunger, or some other member, be rotated to effect the locking function and/or the unlocking function. Alternatively, or additionally, they require that the plunger and the barrel of the syringe be oriented with respect to each other in some requisite orientation. These requirements impose a restriction on the part of the practitioner which it would be desirable not to have.

Furthermore, the looking devices of existing syringes almost universally require extensive modifications of the barrel, and/or the plunger, thus making it impossible to perform simple, relatively inexpensive, modifications to existing syringes in order to add a locking device.

Additionally, the locking devices oftentimes comprise corners or teeth that tend to catch on the surgical gloves used by the practitioner. This, of course, is quite objectionable, even dangerous. Additionally, some syringes tend to draw in a portion of the gloves of the practitioner as the plunger is drawn into the barrel. This is also annoying as the practitioner must disengage such gloves, a practice which may require two hands, perhaps even the assistance of a second person.

OBJECTS AND BRIEF SUMMARY OF THE INVENTION

In view of the problems noted above, it is a principal object of the present invention to provide a syringe that incorporates simple locking means and simple unlocking means that do not require specific relative rotational relationships of the barrel and the plunger. In other words, the locking and unlocking functions can be effected without the necessity of rotating one or the other.

It is a further object of the present invention to provide a syringe that is self-locking, that is the locking function is effected by simply withdrawing the plunger from the barrel to a predetermined desired locking position, at which point the locking occurs automatically without the intervention of the practitioner.

It is a still further object of the present invention to provide a syringe wherein the unlocking function can be effected by the practitioner using only one hand, and that in the position normally required for manipulating the syringe. In other words, it is unnecessary for the practitioner to grasp the syringe, or manipulate it, in some unusual manner.

It is a still further object of the present invention to provide a syringe wherein the locking and unlocking means can be applied to an existing syringe configuration with a minimum of manufacturing modifications, and also wherein such modifications can be effected on a finished syringe as it normally comes from the manufacturing plant.

It is a still further object of the present invention to provide a syringe that provides simple and effective means for the practitioner to grasp and manipulate the syringe with one hand, including performing the functions of locking and unlocking, as described above.

It is a still further object of the present invention to provide a syringe that incorporates means for inhibiting the inadvertent drawing-in of a portion of the practitioner's gloves into the barrel of the syringe when the syringe plunger is being drawn into the syringe barrel due to a vacuum in the barrel.

Briefly summarized, the above objects and advantages are realized in a syringe that incorporates a one-piece, elongate, transparent molded plastic barrel, fashioned from a material such as polypropylene, or other suitable material. The barrel is open at the proximal end and closed at the distal end except for a tubular member passing therethrough, and also includes means for releasably attaching a cannula, or hypodermic needle, or plug thereto.

The plunger comprises an elongate rigid molded shank having a resilient piston head attached at its distal end which slidably and sealingly engages the inner wall of the barrel, thus providing means for a least a partial vacuum to be established in the barrel distal of the piston head.

The means for inhibiting the inadvertent drawing-in of the gloves of the practitioner comprises an annular ridge fashioned around the proximal side of a flange, positioned at the proximal end of the barrel wall, and extending radially and axially with respect to the barrel wall.

The flange positioned at the proximal end of the barrel wall extends radially outwardly, and serves as a force-reacting means for the practitioner to bear his forefinger and thumb against when pushing the plunger in or pulling it out.

The shank is preferably an elongate one-piece molded plastic part, fashioned from a rigid material. It is preferably fashioned with three or four vanes extending radially and axially over the major portion of its length, the vanes configured so as to provide an "X" shaped cross section or a "Y" shaped cross section. This type of configuration minimizes the material used, thus saving weight and cost.

The shank is made long enough that when fully inserted into the barrel there is a tapered portion extending proximally outwardly from the barrel to serve as convenient means for the hand of the practitioner to grasp.

A thumb support is also provided at the proximal end of the shank, configured as a disc with serrations on its proximal face. This serves as a convenient means for the thumb of the user to press against when pushing the plunger into the barrel.

The locking means for locking the plunger in a predetermined position comprises one or more resilient, substantially flat, plate-shaped locking arm(s) which are so configured and positioned that they are pivotally engaged with the shank with an inner edge serving as a pivot axis and an outer edge projecting, in an unstressed mode, slightly outwardly beyond the perimeter of the barrel wall when the plunger is partially withdrawn from the barrel, thus resulting in a constructive interference with the barrel wall, and further wherein the constructive interference is obviated when the locking arm(s) are stressed by being pivoted inward. The locking arm(s) are so positioned that they may be pivoted inward by pressing the thumb and forefinger against them when the syringe is grasped in the normal manner for usage. Preferably only one such locking arm, to be activated by the thumb, is used although there may be two, or even more. Thus, when the plunger is partially withdrawn from the barrel to a predetermined position the locking arm(s) automatically spring out so as to provide constructive interference with the barrel wall, thus locking the plunger in place against being drawn back into the barrel. Thus, a self-locking feature is provided.

The locking arm(s) may be affixed to the shank in any one of several different ways. One such way is to cement them to one or more vanes of the shank in a predetermined position. This method has the advantage that no change at all in the parts of the syringe are required in order to incorporate the locking means. Another way is to fashion a slot or notch in one or more vanes of the shank which cooperates with the locking arm(s) so as to clip and then hold them securely in place, as will be shown in the accompanying drawings.

BRIEF DESCRIPTION OF THE DRAWINGS

Reference is next made to a brief description of the drawings, which are intended to illustrate several different embodiments of the present invention with respect to the manner of making and using the same in its presently understood best mode. The drawings and the detailed description which follow are intended to be merely illustrative and not otherwise limiting of the scope of the invention as set forth in the appended claims.

DETAILED DESCRIPTION OF THE ILLUSTRATED EMBODIMENTS

Figure 1:
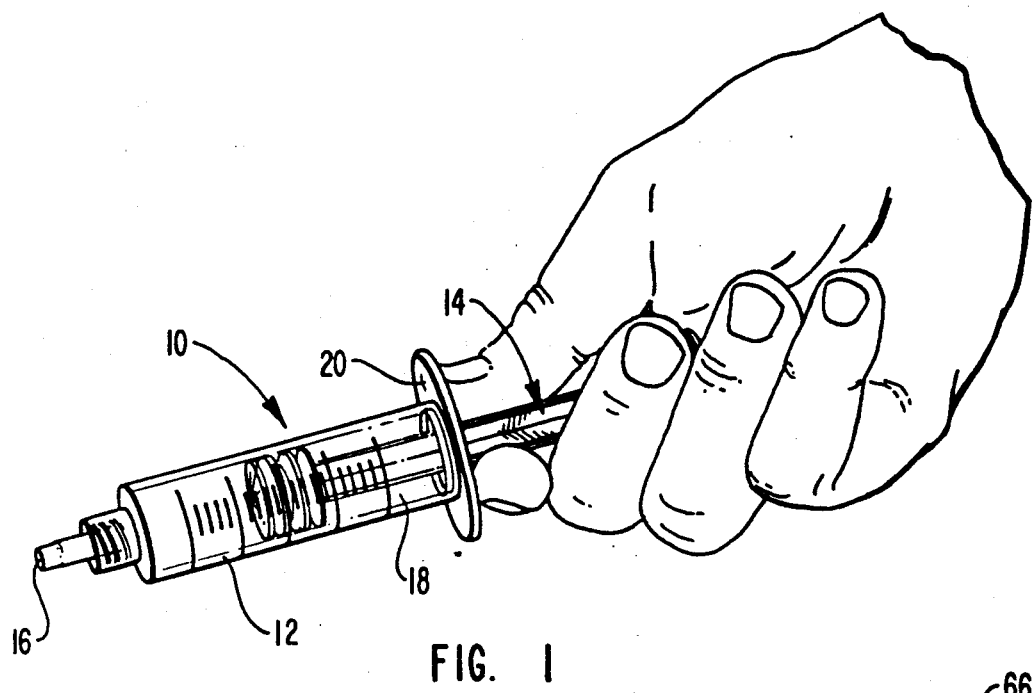
FIG. 1 is a perspective view showing the user grasping the syringe in the palm of his hand and pulling the plunger out of the barrel.

As shown in FIG. 1 the syringe 10 comprises a barrel 12 and a plunger 14. The barrel 12 is preferably a one-piece molded plastic member, fashioned from a transparent plastic, and having a barrel wall 18. The barrel is open at its proximal end and closed at its distal end except for a relatively short tubular member 16 passing therethrough which serves as a means for attaching a cannula thereto.

The barrel also comprises a segmental flange 20 affixed to the proximal end of the barrel and extending radially outward. Although this flange is shown as being segmental, with ears extending outwardly at positions 180° apart, the flange could be completely circular if desired. The flange serves as a means for supporting the fingers when forcing the plunger into the barrel or withdrawing the plunger from the barrel as shown in FIG. 1.

The barrel also has indicia 22 marked thereon which indicate the volume inside the barrel distal of the markings. These markings allow the user to fill the syringe with a prescribed amount of medication, or alternatively to determine when a prescribed amount of fluid has been aspirated from the patient.

Figure 2:
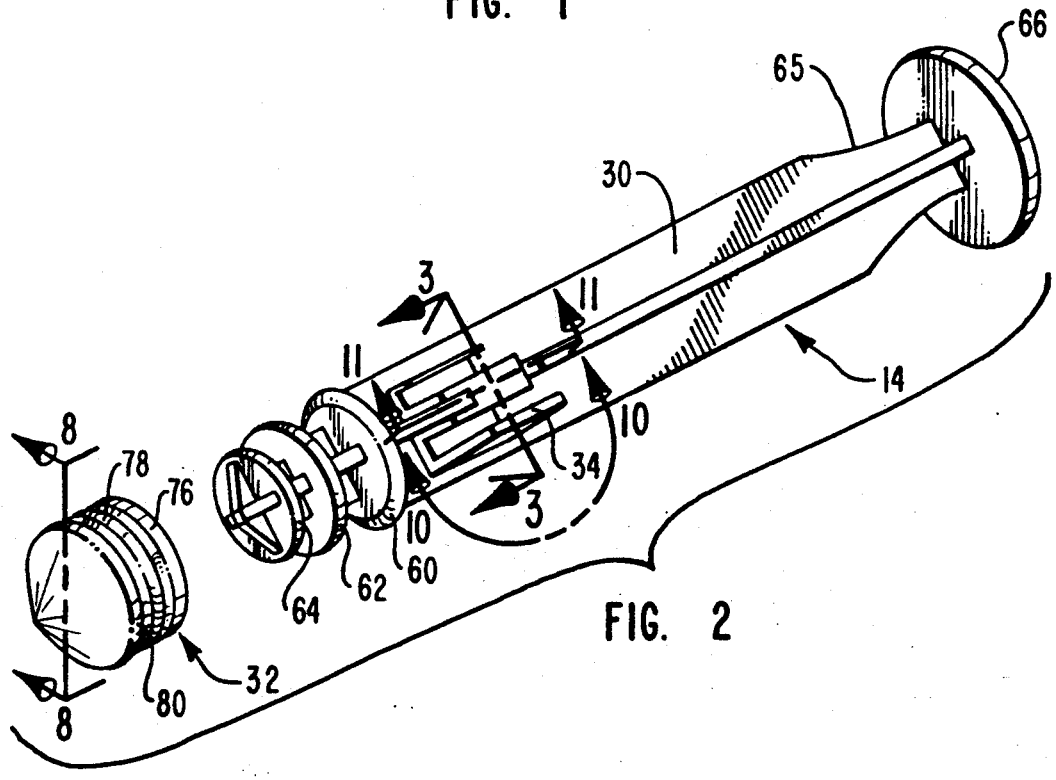
FIG. 2 is an exploded perspective view of the plunger showing the shank and the piston head.

FIG. 2 shows an exploded perspective view of the plunger 14 withdrawn from the barrel. The plunger comprises a shank 30 and a piston head 32, with a locking member 34, to be described later, affixed thereto. The shank 30 is preferably fabricated as a one-piece molded item, fashioned from a rigid plastic. In order to conserve material, and to reduce weight, the shank is configured with a plurality of longitudinal and radially extending vanes. Preferably there are four such vanes, 40, 42, 44, and 46, forming an "X" pattern as shown in cross section in FIG. 3. Alternatively there may be only three, 50, 52, 54, forming a "Y" pattern as shown in cross section in FIG. 5, or even some other number if preferred. These vanes extend longitudinally over the major portion of the shank in order to provide the desired rigidity.

Referring again to FIG. 2 it will be noted that there are preferably three circular discs 60, 62, 64, axially aligned and integral with the shank and positioned near the distal end of the shank. Each of these serves a specific function as explained herein.

Disc 60 has a diameter slightly greater than the diameter of a phantom cylindrical volume that would be generated (swept out) by the vanes of the shank if the shank were rotated about its axis. Additionally, the diameter of disc 60 is slightly less than the inside diameter of the barrel 12, thus permitting it to move axially within the barrel. Disc 60 also serves as a portion of an escape-proof feature, to be described later.

Disc 62 has a diameter slightly less than the diameter of disc 60, being approximately the same as the diameter of the phantom cylindrical volume described above. Disc 62 serves as a bearing surface for the annular rim of piston head 32, to be described later.

Figure 8:
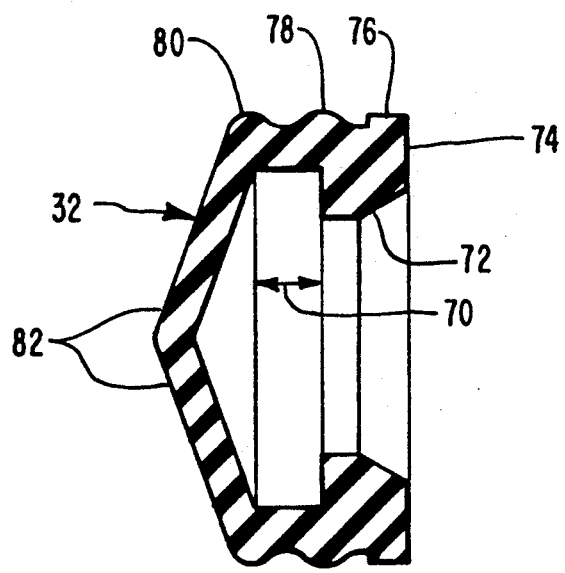
FIG. 8 is a cross sectional view of the piston head.

Disc 64 has a diameter less than the diameter of disc 62 and serves to engage an internal groove 70 of piston head 32, as shown in FIG. 8. Groove 70 has an outer diameter slightly greater than the diameter of disc 62. Piston head 32 has a chamfered portion 72 (see FIG. 8) wherein the smaller diameter of the chamfer is less than the diameter of disc 62. However, piston head 32 is fashioned from a resilient elastic material, such as neoprene rubber, and thus disc 62 can be inserted into groove 70 by expanding the chamfered portion, aided by tilting the disc 64 as it is inserted.

As noted above disc 62 serves as a bearing surface for the piston head 32. Annular surface 74 (FIG. 8) of the piston head 32 is the surface against which disc 62 bears.

Referring again to FIG. 2, still another disc 66 is configured as an integral part of shank 30. Disc 66 is fashioned at the proximal end of the shank and has a diameter somewhat greater than the diameter of the barrel. The primary purpose of disc 66 is to serve as a support for the palm of the user to bear against when the shank is grasped so as to insert or retract the plunger with respect to the barrel. Alternatively, in another mode of usage, it may serve as a support for the thumb of a user to bear against when pushing the plunger into the barrel, in which case the middle finger and index finger of the user bear against the distal surface of the flange 20. The proximal surface of disc 66 is preferably serrated to aid in such usage. Finally, the vanes are tapered at their proximal ends, as shown at 65 for a selected length. This serves to facilitate the grasping of the plunger by the user in the manner shown in FIG. 1, when the plunger is fully inserted into the barrel, permitting the thumb to exert force between the disc 66 and flange 20 to retract the plunger.

Referring again to FIGS. 2 and 8 it can be seen that piston head 32 is equipped with annular ridges 76, 78, 80. These ridges have a diameter slightly greater than the internal diameter of the barrel, and thus, being resilient, serve to sealingly engage the barrel wall. Their purpose is to provide means whereby an at least partial vacuum can be established and maintained for an extended period of time in the barrel distal of the piston head upon retraction of the plunger, as well as providing a fluid-tight seal when the contents of the barrel are injected. End wall 82 (see FIG. 8) of piston head 32 is preferably somewhat tapered so as to form a convex outer surface. The indicia markings on the barrel indicate the volume within the barrel distal of the piston head.

Figure 9:
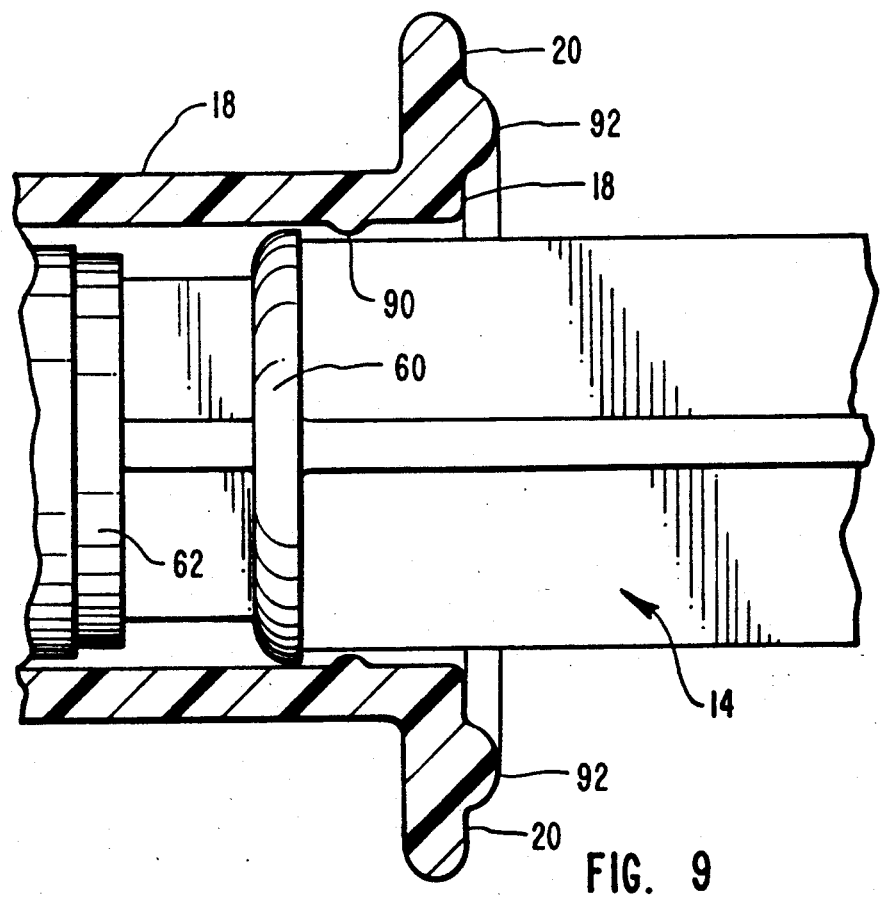
FIG. 9 is a partial cross sectional view of the proximal end of the barrel with the plunger withdrawn approximately to its normal maximum position, short of complete withdrawal, showing the escape-proof feature and the glove-blocking feature.
Figure 10:
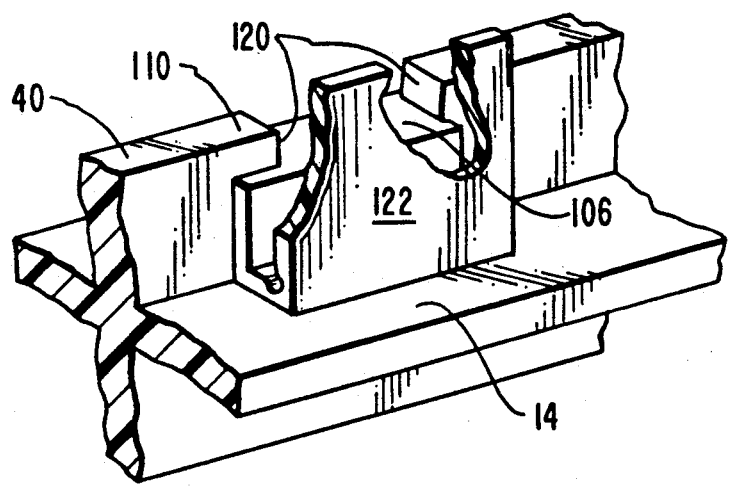
FIG. 10 is cutaway view of a portion of the shank and locking member as indicated in FIG. 2.
Figure 11:
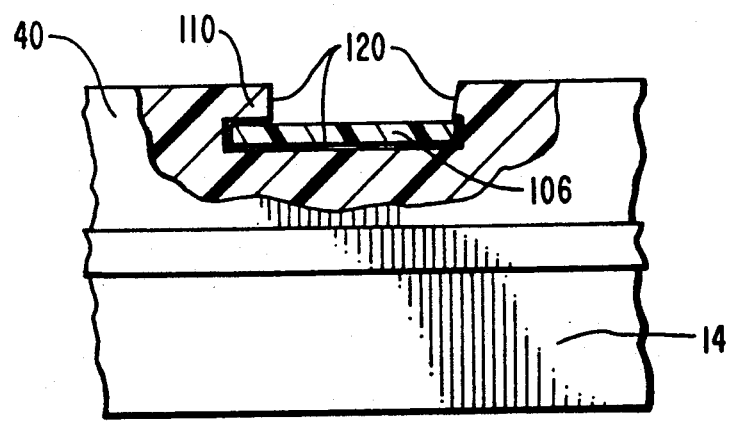
FIG. 11 is a cross sectional view taken along the line 11—11 of FIG. 2.

FIG. 9 shows a partial cross sectional view of the proximal end of the barrel and the plunger inserted therein, but being withdrawn to approximately its outermost position short of being completely withdrawn. As can be seen, and as noted above, disc 60 has a diameter slightly greater than the internal diameter of annular ridge 90 which projects radially inward from the inside wall of barrel 10. Thus, as the plunger 14 is withdrawn to the position where disc 60 interferes with ridge 90 the force necessary to continue the withdrawal becomes greatly increased. This inhibits the user from inadvertently completely withdrawing the plunger. However, due to the resilience of the barrel, complete withdrawal can be effected when necessary by applying sufficient force, aided by a slight tilting of the disc 60. Likewise, the plunger can be initially inserted into the barrel.

As can be seen, there is another annular ridge 92 positioned on the proximal face of the flange 20. In the absence of this ridge 92, when a gloved hand of a user is pressed against flange 20 during usage there is a tendency for a portion of the glove to be drawn into the barrel if there is a vacuum therein which tends to draw the plunger in. However, the presence of the ridge 92 inhibits this drawing-in of the glove by spacing the fingers far enough away from the opening of the barrel to avoid the suction created by the vacuum.

The self-locking feature will be described next. One presently preferred embodiment is shown in FIGS. 2, 3, 10, and 11. As shown best in FIG. 3, this embodiment comprises a relatively short elongate double channel 100, with each individual channel, such as 102 and 104, being configured as a block "U", and with the channels being interconnected by a connecting web 106 which connects the ends of mutually facing, but separated, respective side walls 108 and 110 of the two channels. Web 106 is configured so as to space the facing walls 108 and 110 of the channels a distance apart slightly greater than the thickness of a vane, such as 40, of the plunger's shank, thus allowing the vane 40 to be positioned snugly between the facing walls 108 and 110. Additionally walls 108 and 110 are configured to have a depth approximately the same as the radial dimension of vane 40, all as shown. Thus vane 40 fits snugly between the side walls 108 and 110. Respective webs 112 and 114 of the channels have a width somewhat less than the radial dimension of the vanes 46 and 42. It should also be noted that vane 40 has a slot 120 fashioned therein, as shown best in FIGS. 10 and 11, which accepts web 106 snugly therein. The slot 120 in vane 40 incorporates a projection 110 which projects over web 106, thus serving to lock channel 100 in place.

Figure 3:
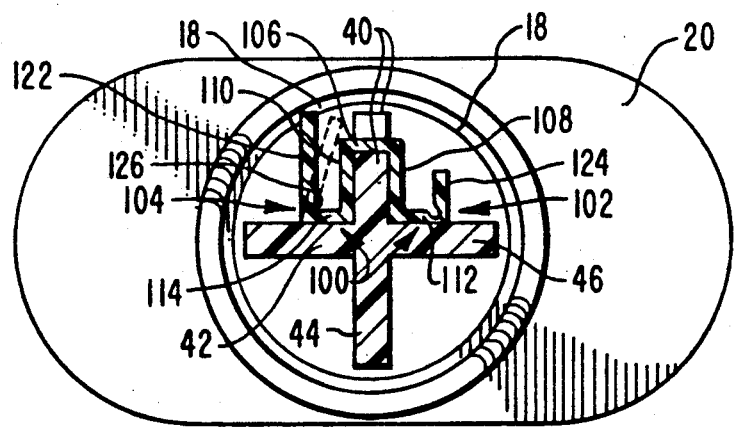
FIG. 3 is a cross sectional view of the shank, taken along the line 3—3 of FIG. 2, also showing the locking member.

Referring to FIG. 3, side wall 122, hereafter called the locking arm, of channel 104 is shown to project a sufficient distance outwardly and away from the vane 40 as to effect constructive interference with the peripheral wall 18 of the barrel. Due to the resilient nature of the channel 100, hereafter called the locking member, the constructive interference may be eliminated by pivoting locking arm 122 inward to a position such as that shown in phantom. Locking arm 122 pivots about its junction 126 with web 114. When so pivoted inward, the plunger with locking member or channel 100 may be inserted into the barrel. Likewise, when the plunger is withdrawn sufficiently far that locking arm 122 is outside the barrel then locking arm 122 springs back into its unstressed position, again effecting constructive interference which prevents the plunger from being pulled back into the barrel. Thus, a self-locking feature is provided.

Figure 4:
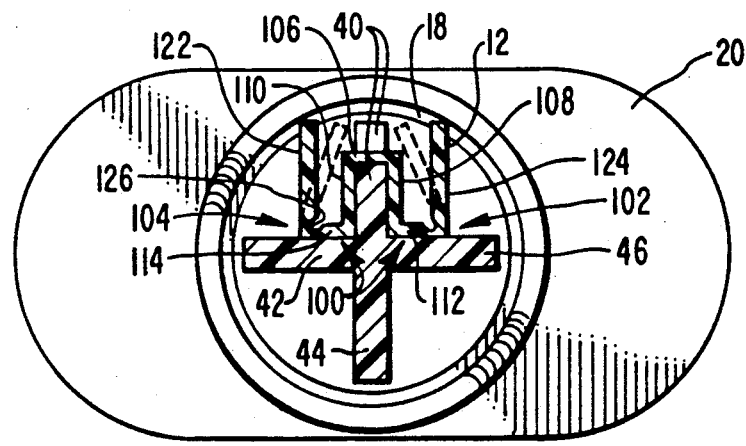
FIG. 4 is a cross sectional view corresponding to FIG. 3 except with an alternative locking member.

It should be noted that sidewall 124 may also be configured as a locking arm so as to provide constructive interference with the peripheral barrel wall simply by extending its dimension as was done for locking arm 122, as shown in FIG. 4. This variation may be preferred by some users as it provides a double locking feature.

It should also be noted that the pivoting action may be enhanced by providing a slight relief cutout 126 at the junction of the locking arm 122 and web 114, as depicted.

It should further be noted that a plurality of slots 120 on vane 40 (see FIG. 10) could be provided, each having a locking member so as to permit the plunger to be locked at any location along the plunger.

Figure 5:
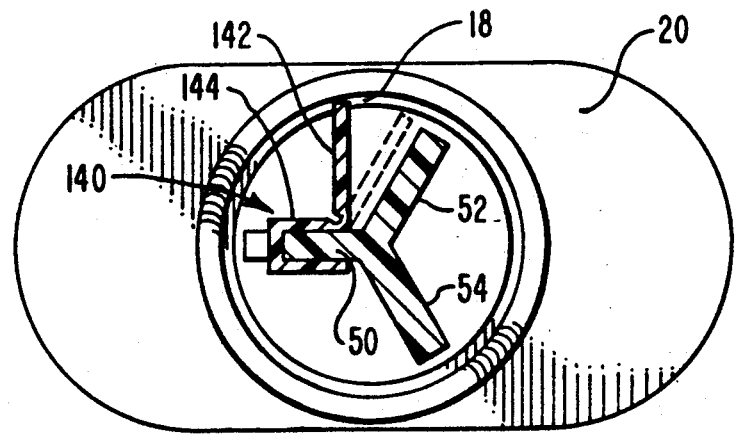
FIG. 5 is a cross sectional view of an alternative embodiment of the shank, and also an alternative locking member.

The embodiment described above utilizes a plunger with a shank having four vanes. Another embodiment utilizing a shank having three vanes is depicted in FIG. 5. The locking member 140 is configured as a channel having a projecting arm 142, hereafter called a locking arm which serves the same function as locking arm 122 of the previous embodiment of FIG. 3. Locking arm 142 pivots about a junction 143 which comprises the junction of looking arm 142 with sidewall 144. In its unstressed position locking arm 142 projects outwardly sufficiently far as to provide constructive interference with peripheral wall 18 of the barrel, as noted, when the plunger is sufficiently withdrawn. Thus, a self-locking feature is provided similar to the other embodiment. Unlocking is effected by pivoting locking arm 142 inward to a position as noted by the phantom lines. Locking member 140 is affixed to vane 50 of the shank in the same manner as locking member 100 of the previous embodiment. Alternatively, locking member 140 may be cemented to vane 50.

Figure 6:
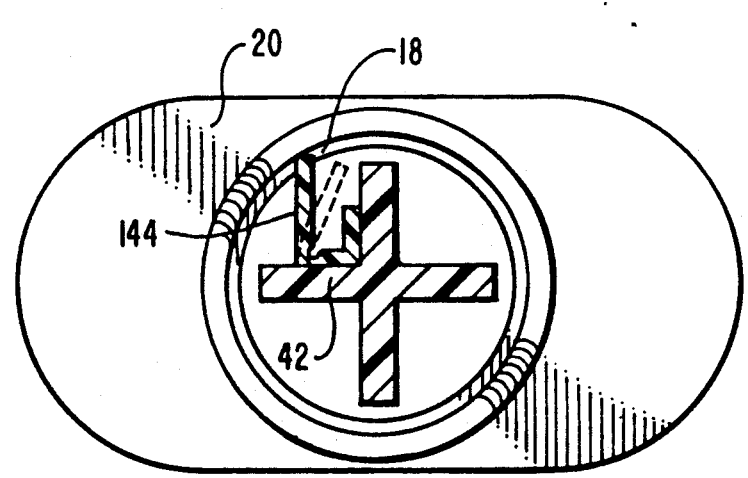
FIG. 6 is a cross sectional view of an alternate embodiment of the locking member cemented in place.
Figure 7:
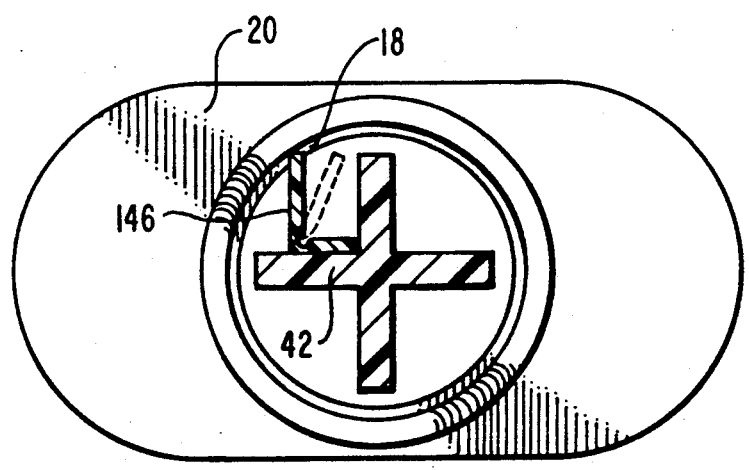
FIG. 7 is a cross sectional view of an alternate embodiment of the locking member cemented in place.

In addition to the above described embodiments of the locking member other shapes could be employed, such as a single "U" shaped channel 144, as shown in FIG. 6, or an "L" shaped member 146 as shown in FIG. 7. Such members would preferably be affixed to the shank by cementing. It will of course also be apparent that any of the embodiments as illustrated and described could also be formed by molding them as a part of the shank of the syringe plunger. It is to be understood that all such shapes are considered to be merely simple variations of this invention, and are within the spirit and scope of the invention.

Broadly speaking, the invention teaches the use of any locking member that comprises a resilient locking member attached to the shank of a syringe plunger, and wherein the locking member is configured to pivot into the volume of space of the syringe barrel when the locking arm is pivoted inward by a user, and wherein the locking arm reverts back to its unstressed locking position when pulled outside of the barrel.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A syringe apparatus comprising:
   (a) an elongate barrel having a peripheral wall, the barrel being open at its proximal end;
   (b) an elongate plunger axially movable in both proximal and distal directions in the barrel through the opening at said proximal end of the barrel; and
   (c) self-activated, resilient locking means attached to said plunger for locking the plunger in a predetermined longitudinal position relative to the barrel, said locking means being slidably moveable in both proximal and distal directions while situated within the barrel, and said locking means springing into an open position so as to engage the peripheral wall of said barrel when withdrawn from the barrel, in any rotational orientation whereby said plunger is then prevented from being pulled or pushed into said barrel, and said locking means responding to an applied force that disengages the locking means from the peripheral wall of said barrel to unlock the syringe plunger and permit re-entry of the plunger into the barrel and subsequent sliding of the plunger within the barrel in either of the proximal or distal directions.

2. A syringe apparatus as defined in claim 1 wherein the locking means comprises an elongate locking arm, fashioned from a resilient material, pivotally engaged with the plunger at a position intermediate the length of the plunger.

3. A syringe apparatus as defined in claim 1 wherein the locking means comprises a locking member comprising a resilient, substantially flat, plate-shaped locking arm positioned when the plunger is inserted into the barrel within the confines of a cylindrical volume of space as defined by the peripheral wall of the barrel, a pivot point about an inner edge thereof, and further comprising an outer edge which projects beyond the perimeter of the volume of space when withdrawn from the barrel, and wherein the outer edge of the locking arm pivots into the volume of space so as not to project beyond the perimeter when the locking arm is pivoted inward by a force exerted on the locking arm.

4. A syringe apparatus as defined in claim 1 wherein said plunger comprises a plurality of longitudinal vanes.

5. A syringe apparatus as defined in claim 4 wherein said self-activated resilient means comprises an elongate locking arm pivotally mounted to a vane of said plunger.

6. A syringe apparatus as defined in claim 5 wherein said locking arm is bonded to said vane.

7. A syringe apparatus as defined in claim 5 wherein one of said vanes is notched and wherein said locking resilient means further comprises means for snapping said locking arm into said notch of said vane.

8. A syringe apparatus as defined in claims 1 or 2 wherein said barrel comprises:
   a flange positioned at the opening of the proximal end of the barrel; and
   an annular ridge formed on said flange around at least a portion of the opening.

9. A syringe apparatus as defined in claim 4 wherein said vanes are each tapered at a proximal end thereof to accommodate placement of a thumb and forefinger about said tapered ends.

10. A syringe apparatus comprising:
   (a) an elongate cylindrical barrel having a peripheral wall, the barrel being open at its proximal end and closed at its distal and except for a tubular member passing therethrough;
   (b) an elongate plunger axially movable within the barrel in both proximal and distal directions comprising:
       (i) an elongate shank comprising a plurality of axially and radially extending vanes along at least a portion of the shank's length; and
       (ii) a piston head affixed to a distal end of the shank and engaging the peripheral wall of the barrel in a fluid-tight manner; and
   (c) releasable self-locking means slidably moveable in both proximal and distal directions while the locking means is situated within the barrel, and said releasable self-locking means locking the plunger in a predetermined longitudinal position relative to the barrel, said releasable self-locking means comprising at least one outwardly extending resilient member affixed to a vane of the shank at a pivot point so as to lock the plunger in said predetermined position when the plunger has been retracted to a position where said resilient member is outside of the barrel, in any rotational orientation and wherein the resilient member permits reinsertion of the plunger into the barrel when pivoted inwardly about said pivot point and subsequent sliding of the plunger within the barrel in either of the proximal or distal directions.

11. A syringe apparatus as defined in claim 10 wherein said resilient member is bonded to a vane of said shank.

12. A syringe apparatus as defined in claim 10 wherein one of said vanes is notched and wherein said self-locking means further comprises means for snapping said resilient member into said notch of said one vane.

13. A syringe apparatus as defined in claim 10 wherein said barrel comprises:
   a flange positioned at the opening of the proximal end of the barrel; and
   an annular ridge formed on said flange around at least a portion of the opening.

14. A syringe apparatus as defined in claim 10 wherein said vanes are each tapered at a proximal end thereof to accommodate placement of a thumb and forefinger about said tapered ends.

* * * * *

UNITED STATES PATENT AND TRADEMARK OFFICE
CERTIFICATE OF CORRECTION

PATENT NO. : 5,215,536
DATED : June 1, 1993
INVENTOR(S) : FRED P. LAMPROPOULOS et al.

It is certified that error appears in the above-identified patent and that said Letters Patent is hereby corrected as shown below:

Column 1, line 16, "preparation" should be --preparing--
Column 1, line 42, "o" should be --of--
Column 2, line 20, "looking" should be --locking--
Column 9, line 6, delete "self-activated resilient" and insert --locking--
Column 9, line 15, delete "resilient"
Column 9, line 31, "and" should be --end--

Signed and Sealed this

Fifteenth Day of March, 1994

BRUCE LEHMAN

Attest:

Attesting Officer

Commissioner of Patents and Trademarks